(12) United States Patent
Becker et al.

(10) Patent No.: US 6,899,667 B2
(45) Date of Patent: May 31, 2005

(54) METHOD AND APPARATUS FOR THE TREATMENT OF PHYSICAL AND MENTAL DISORDERS WITH LOW FREQUENCY, LOW FLUX DENSITY MAGNETIC FIELDS

(76) Inventors: Paul F. Becker, 16 E. Highpoint Rd., Stuart, FL (US) 34996; Bruce E. Richardson, 1357 NE. Ocean Blvd., Stuart, FL (US) 34996

(*) Notice: Subject to any disclaimer, the term of this patent is extended or adjusted under 35 U.S.C. 154(b) by 88 days.

(21) Appl. No.: 10/278,109

(22) Filed: Oct. 21, 2002

(65) Prior Publication Data

US 2004/0077921 A1 Apr. 22, 2004

(51) Int. Cl.[7] .............................. A61N 2/00; H01F 21/04
(52) U.S. Cl. ............................................ 600/9; 336/122
(58) Field of Search ..................................... 600/9, 13–15, 600/527; 687/50, 51; 336/122, 230, 90; 204/155, 157.15; 435/173.5; 128/898

(56) References Cited

U.S. PATENT DOCUMENTS

| | | | | |
|---|---|---|---|---|
| 4,266,533 A | * | 5/1981 | Ryaby et al. .................. 128/1.5 |
| 4,428,366 A | | 1/1984 | Findl et al. .................... 128/15 |
| 4,548,208 A | * | 10/1985 | Niemi ........................... 600/14 |
| 4,550,714 A | * | 11/1985 | Talish et al. ................... 600/14 |
| 4,587,957 A | * | 5/1986 | Castel ............................ 600/9 |
| 4,616,629 A | * | 10/1986 | Moore ........................... 600/13 |
| 4,674,482 A | * | 6/1987 | Waltonen et al. ............. 128/1.5 |
| 4,889,526 A | * | 12/1989 | Rauscher et al. .............. 600/14 |
| 4,940,453 A | * | 7/1990 | Cadwell ......................... 600/13 |
| 5,014,699 A | * | 5/1991 | Pollack et al. ............ 128/419 F |
| 5,030,196 A | * | 7/1991 | Inoue ............................ 600/14 |
| 5,116,304 A | * | 5/1992 | Cadwell ......................... 600/13 |
| 5,192,263 A | * | 3/1993 | Kraus ............................ 600/14 |
| 5,215,633 A | * | 6/1993 | Liboff et al. .................. 204/155 |
| 5,224,922 A | * | 7/1993 | Kurtz ............................ 600/13 |
| 5,338,286 A | * | 8/1994 | Abbott et al. .................. 600/14 |
| 5,368,544 A | | 11/1994 | Tran et al. ...................... 600/9 |
| 5,415,617 A | * | 5/1995 | Kraus ............................ 600/13 |
| 5,441,495 A | * | 8/1995 | Liboff et al. .................... 600/9 |
| 5,496,258 A | * | 3/1996 | Anninos et al. ............... 600/13 |
| 5,518,495 A | * | 5/1996 | Kolt .............................. 600/13 |
| 5,665,049 A | * | 9/1997 | Markoll ......................... 600/14 |
| 5,669,868 A | * | 9/1997 | Markoll ......................... 600/14 |
| 5,752,911 A | * | 5/1998 | Canedo et al. .................. 600/9 |
| 5,769,970 A | * | 6/1998 | Robelet et al. ............... 148/320 |
| 5,813,970 A | * | 9/1998 | Abrams et al. ................ 600/14 |
| 5,842,966 A | * | 12/1998 | Markoll ......................... 600/14 |
| 6,048,302 A | * | 4/2000 | Markoll ......................... 600/13 |
| 6,086,525 A | * | 7/2000 | Davey et al. .................. 600/13 |
| 6,099,459 A | * | 8/2000 | Jacobson ....................... 600/13 |
| 6,123,658 A | * | 9/2000 | Schweighofer et al. ....... 600/13 |
| 6,132,361 A | * | 10/2000 | Epstein et al. ................. 600/13 |
| 6,162,166 A | * | 12/2000 | Neuwirth ....................... 600/14 |
| 6,203,486 B1 | * | 3/2001 | Miller et al. .................... 600/9 |
| 6,210,317 B1 | * | 4/2001 | Bonlie ............................ 600/9 |
| 6,263,878 B1 | * | 7/2001 | Litovitz ....................... 128/897 |
| 6,280,376 B1 | * | 8/2001 | Holcomb ....................... 600/13 |
| 6,425,852 B1 | * | 7/2002 | Epstein et al. ................. 600/13 |
| 2001/0003799 A1 | * | 6/2001 | Boveja .......................... 607/45 |
| 2002/0103411 A1 | * | 8/2002 | Bailey et al. ................... 600/9 |

FOREIGN PATENT DOCUMENTS

EP 0181053 5/1986
GB 2219210 12/1989

* cited by examiner

*Primary Examiner*—Eric F. Winakur
*Assistant Examiner*—Nikita R. Veniaminov
(74) *Attorney, Agent, or Firm*—Holland & Knight LLP

(57) ABSTRACT

A method and apparatus comprises a circuit adapted to be coupled to a power supply which produces a pulsed DC output, and a magnetic field generating coil coupled to the output of the circuit which is effective to produce a time varying magnetic field having a flux density in the range of about 0.0001 to 2.0 gauss at a frequency in the range of about 0 to 45 Hz. The coil is positioned at or near the site on the body of the patient to be treated, or, alternatively, beneath the patient's sleeping surface for a period ranging from about one-half hour to several hours depending upon the method and condition to be treated.

21 Claims, 3 Drawing Sheets

METHOD AND APPARATUS FOR THE TREATMENT OF PHYSICAL AND MENTAL DISORDERS WITH LOW FREQUENCY, LOW FLUX DENSITY MAGNETIC FIELDS

FIELD OF THE INVENTION

This invention relates generally to a method and apparatus for the treatment of physical and mental disorders, and, more particularly, to a portable device capable of being operated safely and effectively by patients which produces a time varying, magnetic field having a low frequency and low flux density effective in the treatment of a wide variety of physical and mental disorders.

BACKGROUND OF THE INVENTION

Magnetic fields have long been used for the treatment of physical injuries and chronic pain. Early magnetic therapy involved the use of static magnetic fields produced by permanent magnets incorporated into items such as bracelets, belts, back pads, mattress pads and mattresses. It is believed that static magnetic fields have some efficacy in the treatment of broken bones and soft tissue injuries, and tend to promote the circulation of blood as well as relieve stiffness in muscles. The effectiveness of such treatments in human and veterinary applications has been the subject of debate.

More recent attempts to employ the therapeutic effects of magnetic fields have focused on devices which generate an electromagnetic field, and the methods of treatment employing such devices. Although a variety of designs have been proposed in the prior art, electromagnetic devices generally comprise a power supply coupled to a circuit capable of producing an AC or DC output which is transmitted to an inductor coil. One form of inductor coil consists of a number of wire windings wrapped about a coil body with an open or air center, or, alternatively, a ferrous core wrapped with wire windings. In response to the output from the circuit, an electromagnetic field is generated by the inductor coil which is then directed toward the area(s) of the body of a patient to be treated.

In many instances, the circuit of electromagnetic devices produces a pulsed or time-varying output in the shape of a square wave, sine wave, triangular wave or the like. Such output can be at essentially any selected frequency and voltage. A pulsed output from the circuit results in the production of a time-varying or pulsed magnetic field by the inductor coil. If the circuit emits an AC signal, the position of the north and south poles of the resulting magnetic field from the inductor coil changes with each cycle, whereas a DC output produces an electromagnetic field in which the position of the magnetic poles remains constant.

The application of the general concepts of the formation of electromagnetic fields noted above to the treatment of physical and mental disorders has resulted in a widely varying array of devices and treatment methods. Prior art devices operate at completely different ends of the spectrum in terms of field strength and frequency. The predominant approach appears to follow the adage that "more is better." U.S. Pat. Nos. 6,425,852; 6,132,361; 5,813,970 and 5,769,778, for example, teach electromagnetic devices which produce a magnetic field having a flux density in range of up to 10,000 to 20,000 gauss. Devices of this type are used for therapies such as transcranial magnetic brain stimulation for the treatment of neurological and mental disorders. On the other end of the spectrum, devices have been developed for the treatment of various conditions using a magnetic field having a flux density in the range of 10 nanogauss to 10 milligauss, applied at frequencies in the range of 0 to 1000 Hz. See, for example, U.S. Pat. Nos. 6,099,459 and 5,496,258.

There appears to be no consensus whatsoever as to what flux density levels or frequencies should be employed in electromagnetic therapy. Although proposed as a non-invasive alternative to pharmacological and nutritional solutions, it is believed that electromagnetic therapy conducted at the high flux density and/or high frequency levels noted above may, in fact, be harmful whereas treatment at the lower end of the spectrum as suggested in U.S. Pat. No. 6,099,459 will have little, if any, therapeutic effect without extensive technical expertise. None of these treatment methods are reflective of the magnetic field density levels and frequencies which occur naturally within a patient, or are produced naturally within the ionosphere and by the earth.

Other significant limitations of many prior art therapeutic electromagnetic devices is their lack of portability, their complexity and the need for relatively skilled medical personnel to operate them effectively. For example, U.S. Pat. Nos. 6,280,376; 6,099,459; 6,210,317 and application U.S. Pat. No. 2002/0103411 disclose devices which are not portable and require a skilled technician or physician to operate. In order to receive treatment, patients must undertake the time and expense of traveling to the office where the machine is located during normal business hours. Other devices, while they may be more portable, permit a relatively wide range of adjustment of field strength and/or frequency. Allowing patients and practitioners to control these parameters, even with prior instruction, can lead to ineffective or potentially harmful treatment.

SUMMARY OF THE INVENTION

It is therefore among the objectives of this invention to provide a method and apparatus for the treatment of physical and mental disorders with electromagnetic therapy which does not require skilled personnel to administer, which is portable, which operates at naturally occurring magnetic field strengths and frequencies, which limits the extent of operating adjustments permitted on the part of a patient or practitioner and which is capable of treating a wide variety of physical and mental disorders in human or animal subjects.

These objectives are accomplished in the instant method and apparatus comprising a circuit adapted to be coupled to a power supply which produces a pulsed DC output, and a magnetic field generating coil coupled to the output of the circuit which is effective to produce a time varying magnetic field having a flux density in the range of about 0.0001 to 2.0 gauss at only specific frequencies which occur naturally within the patient or are naturally occurring terrestrially in the range of about 0 to 45 Hz. The coil is positioned at or near the site on the body of the patient to be treated, or, alternatively, beneath the patient's sleeping surface, for a period ranging from about one-half hour to several hours depending upon the condition or method used for treatment.

An important aspect of this invention is predicated upon the concept that naturally occurring magnetic fields, both in terms of flux density and frequency, have beneficial therapeutic effects on a wide variety of physical and mental conditions. It is known that the geomagnetic field strength of the earth is about 0.3 to 0.6 gauss, and that such magnetic field exists terrestrially in the atmosphere and geomagnetically from the earth itself. What has not been recognized prior to the present invention is the beneficial effects of electromagnetic therapy applied at flux density and frequency levels which closely approximate those occurring naturally. It has been found that psychiatric and neurological disorders, central nervous system disorders, tissue damage, orthopedic conditions, wounds, muscle stiffness and a variety of conditions which cause pain and chronic pain all can be safely and effectively treated with a DC, time varying electromagnetic field whose flux density and frequency approximate that which are naturally occurring.

The device of the instant invention is portable and can be readily and safely operated by patients at home or work without the presence of medical personnel. It consists of a housing which contains a circuit operable to produce a pulsed, DC output having a wave form such as square, triangular, sine or the like. In one embodiment, the housing is provided with an on/off switch and the frequency of the output is fixed at one level by the circuitry at for instance 9.6 Hz, as this frequency is particularly effective overall. Alternatively, the housing includes an adjustment knob or the like connected to a potentiometer in the circuit for adjustment of the frequency of the output from the circuit. In still another embodiment, a microprocessor is incorporated in the circuitry which is programmable to sequentially vary the output frequency of the circuit to selected frequencies in the range of 0.5 to 45 Hz.

In all embodiments, an inductor coil, e.g. a magnetic field generating coil, is coupled to the output of the circuit. The coil can be in the form of a wire winding about a coil body having an open or air core, or a ferrous core about which the wire is wound. As described below, the two coils are used for different types of treatments in accordance with the method of this invention.

DESCRIPTION OF THE DRAWINGS

The structure, operation and advantages of the presently preferred embodiment of this invention will become further apparent upon consideration of the following description, taken in conjunction with the accompanying drawings, wherein.

DETAILED DESCRIPTION OF THE PREFERRED EMBODIMENTS

Figure 1:
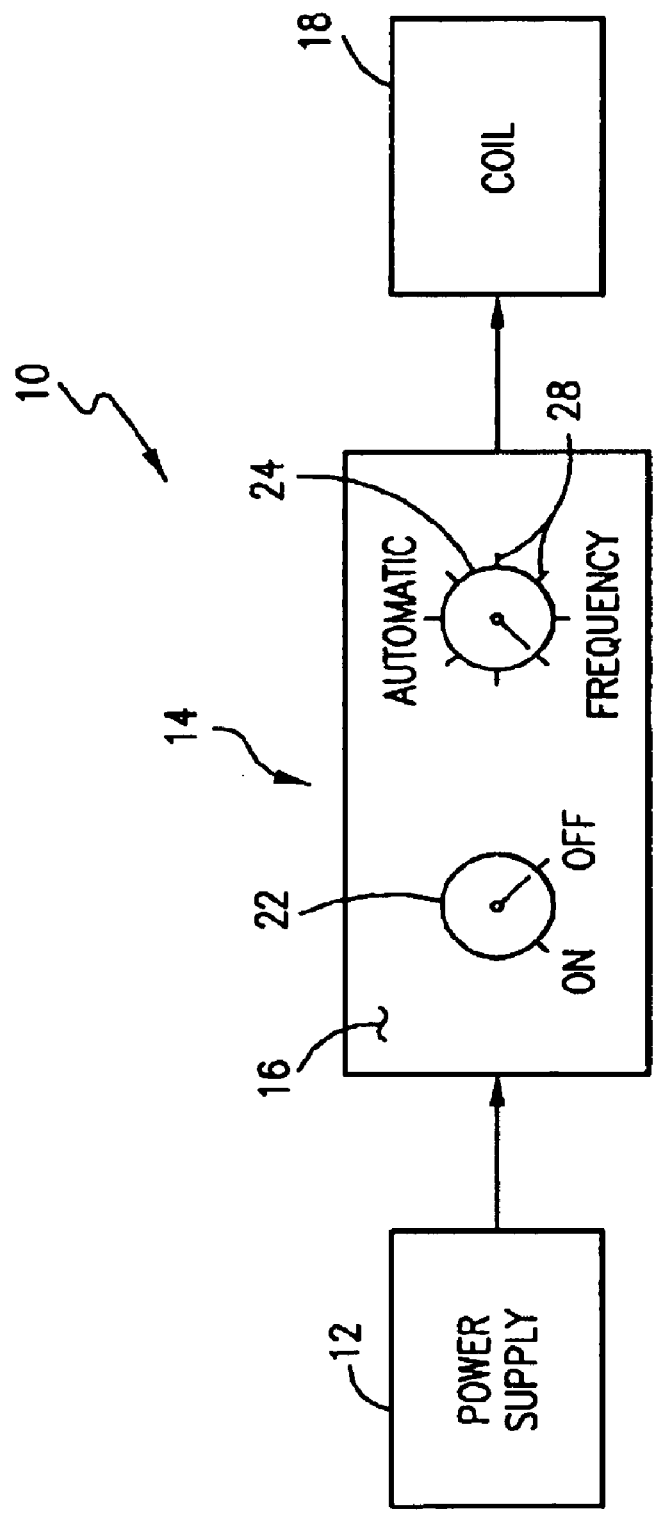
FIG. 1 is schematic illustration of the electromagnetic device of this invention.

Referring now to the drawings, FIG. 1 is a diagrammatic depiction of the electromagnetic device 10 of this invention which comprises a power supply 12, and housing 14 having a control panel 16 and a magnetic field generating or inductor coil 18. The power supply 12 is shown as being coupled to the housing 14, but it should be understood that the power supply could be incorporated within the housing 14 in the form of a battery pack using preferably a rechargeable battery (not shown). Alternatively, the power supply 12 can take the form of a transformer which would plug in to a wall socket and step down 120/240 volt supply to voltage for use in the circuit 20 described below in connection with a discussion of FIG. 2.

The housing 14 is shown with a control panel 16 for purposes of illustration. In one embodiment of this invention, the control panel 16 includes only an on/off switch 22 which would turn on the circuit 20 allowing the coil 18 to produce a magnetic field at a predetermined, fixed flux density and frequency. Alternatively, the control panel 16 is provided with a control knob 24 coupled to a potentiometer 26 included within the circuit 20, as described below in connection with a discussion of FIG. 2, to permit variation of the output frequency of the circuit 20, and, hence, the frequency of the magnetic field produced by the coil 18. The control knob 24 may be adjusted manually to selected frequency settings, represented by the radial lines 28 on the control panel 16, or, alternatively, to an "automatic" setting in which a programmable microprocessor 30 within the circuit 20 is activated to sequentially vary the output frequency of the circuit 20, as described below.

Figure 2:
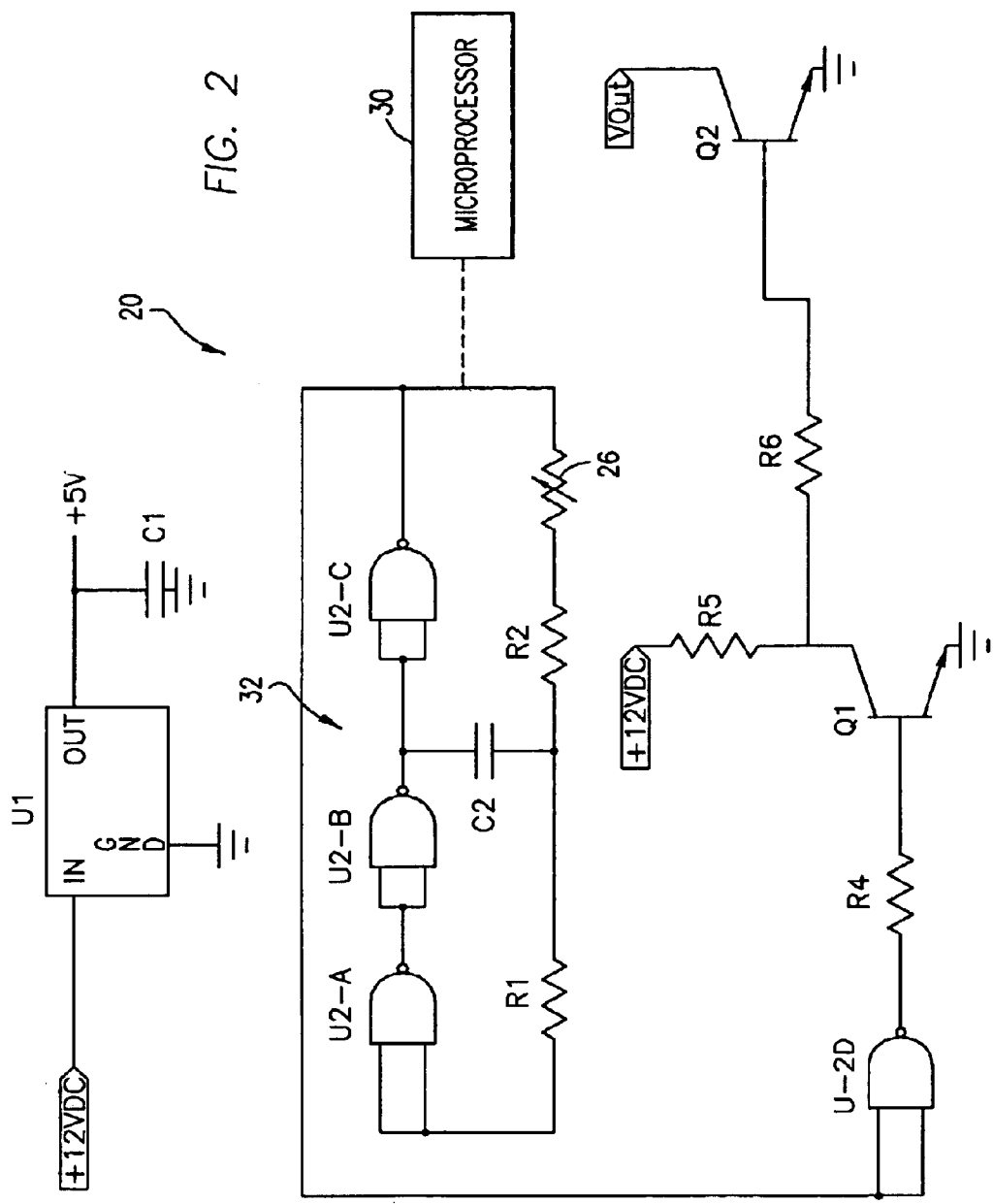
FIG. 2 is a diagram of the circuit of the device in FIG. 1.

Referring now to FIG. 2, the circuit 20 contained within the housing 14 is shown coupled to the power supply 12 which includes an IC voltage regulator U1 and a filter capacitor C1. The power supply 12 provides a voltage output of 5 volts to an astable multivibrator 32 consisting of NAND gates U2-A, U2-B, U2-C, resistors R1 and R2, capacitor C2 and the potentiometer 26. The operating frequency of the astable multivibrator 32 is determined by the values of R1, R2, potentiometer 26 and capacitor C2, which can be varied over a range of 0.5 Hz to 45 Hz by operation of the potentiometer 26.

As schematically depicted with a phantom line in FIG. 2, the circuit 20 may optionally include a microprocessor. As noted above, the microprocessor 20 is operative to sequentially vary the frequency output of the astable multivibrator 32. The selected frequencies over which the output is varied are discussed below in connection with the description of a particular treatment method in accordance with this invention.

The signal from the astable multivibrator 32 is input to the NAND gate U2-D which is configured as an inverter. U2-D is connected through resistor R4 to and NPN bipolar junction transistor Q1 configured as an emitter follower to serve as a level shifter, e.g. to convert the signal from 5 volts to the output voltage used in one embodiment or another. Q2 is an NPN bipolar junction transistor which is coupled to Q1 through resistors R5 and R6. It functions to invert the signal from Q1, thus producing a pulsed or time varying DC output signal in the range of 0.5 to 45 Hz. When the output signal is coupled to the coil 18, a pulsed magnetic field is produced having a flux density in the range of 0.0001 to 2 gauss depending upon the embodiment of the device 10 and the size of the coil 18 which is coupled to the device at a frequency of 0.5 to 45 Hz. Since a DC output signal is provided to the coil 18 by the circuit 20, the north and south poles of the resulting magnetic field do not vary in position relative to the coil 18.

Figure 3:
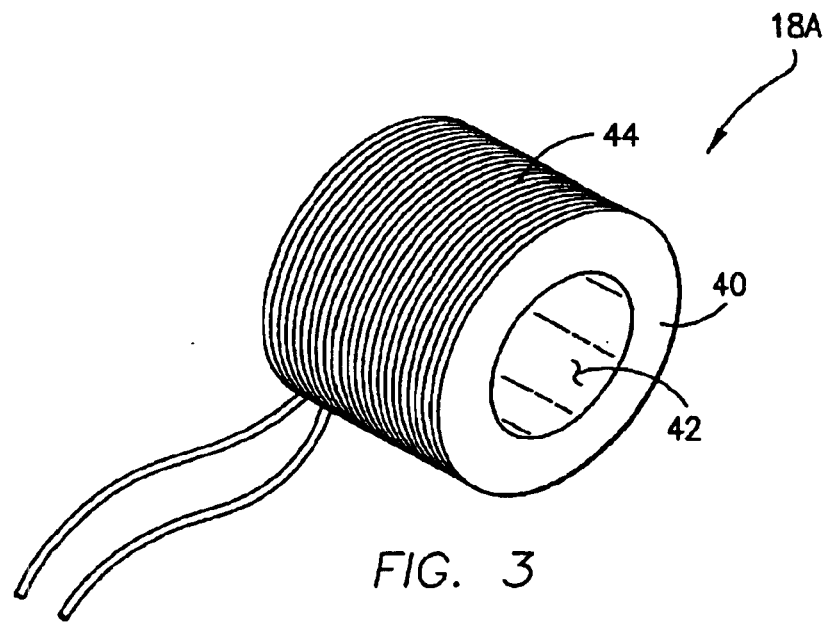
FIG. 3 is a schematic view of an open center coil employed in the subject device.
Figure 4:
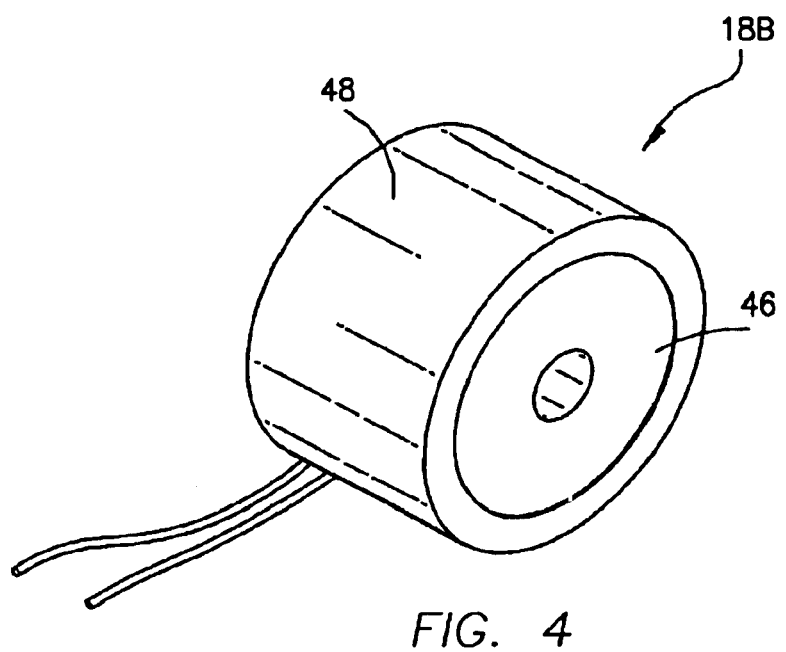
FIG. 4 is a view similar to FIG. 3 of an alternative coil with a ferrous center.

With reference to FIGS. 3 and 4, two basic types of coil 18 are shown which are employed in the device 10 of this invention. The coil 18A of FIG. 3 includes a coil body 40 with an open center or core 42 around which receives a wire winding 44. The coil body 40 is schematically depicted in FIG. 3 with a cylindrical shape, but it may take the form of a flat disc in the general shape of a donut. The diameter of the coil body 40 and its thickness can vary, and is chosen to accommodate a particular treatment therapy, as described below. Alternatively, a coil 18B is employed in the method of treatment herein as shown in FIG. 4. The coil 18B is a standard electromagnet having a ferrous core 46 which carries a wire winding (not shown) enclosed within a metal jacket 48. Coils 18B of this type are commercially available from A.P.W. Co. Inc. of Rockaway, N.J.

The device 10 of this invention has been successfully employed in treating a number of different conditions. The configuration of the device 10, method of treatment and related case studies for different types of disorders or conditions are discussed in separate sections below.

Psychiatric, Neurological and Central Nervous System Disorders

In one embodiment of the method of this invention, the device 10 is used to apply repetitive transcranial magnetic stimulation ("rTMS") to the back, frontal portion or other areas of the head. It is believed that the application of a pulsed, DC electromagnetic field, at the flux density and frequency ranges noted above and discussed in more detail below, is a novel approach to brain wave entrainment which has the attendant benefits of reducing errant brain wave activity and stimulating certain neurological processes. When applied to the frontal brain regions, rTMS therapy performed with the device 10 herein has an upmodulatory effect on both the mesolimbic and mesostriatal dopaminergic systems. An increase in dopaminergic neurotransmission may contribute to the beneficial effects of rTMS in the treatment of psychiatric and neurological disorders. Further, rTMS performed according to this invention synchronies the circadian rhythm and neuroendocrine functions of the pineal, hypothalamus and pituitary glands.

The pineal gland, which has been found to be particularly sensitive to magnetic fields, regulates the function of the pituitary, thyroid and adrenal glands through the production of several neurochemical agents. It also affects the central nervous system and immune system via the production of melatonin. Melatonin has been found to be a potent antioxidant and free radical scavenger with anti-aging, anti-mutagenic and oncostatic properties. In pathologies wherein high production of free radicals is a primary cause of disease, melatonin is protective of mitochondrial damage due to oxidative stress, thereby protecting against impaired mitochondrial production of adenosine tri-phosphate ("ATP"), the fuel that fires all cellular processes. Melatonin is also useful in combating oxidative neurotoxicity which is associated with several acute and chronic neurodegenerative diseases. It has been shown to possess anti-inflammatory effects and reduces tissue destruction during inflammatory reaction. Melatonin attenuates transendothelial cell migration and edema which contribute to tissue damage by reducing the regulation of a variety of proinflammatory cytokines.

In order to perform therapeutic treatment on a selected area of the head, the device 10 is employed with an air core coil 18A positioned proximate the head, e.g. about 5 to 10 centimeters away from the head, beneath a pillow or other padding for comfort. The patient can be placed in a prone or reclined seated position, or lying flat on a surface. In most instances, it is preferable to place the coil 18A at the back of the head, although it may be located proximate any specific area exhibiting symptoms to be treated. The pulsed, DC output from circuit 20 results in a time varying magnetic field from the coil 18A whose north and south poles remain in the same position relative to the coil 18A. With a flux density level at the coil 18A of in the range of about 0.5 to 1 gauss, and the coil 18A positioned at the back of the head, the flux density at the back of the patient's head is typically on the order of about 0.01 to 0.4 gauss, and preferably in the range of about 0.01 to 0.1 gauss. The flux density at the subthalmic region of the brain slightly slower.

In the method of treatment employing rTMS according to this invention, the device 10 is operated using the control knob 24 to vary frequency settings to approximate those of the delta, theta, alpha and beta frequencies of the brain. In the manual mode of operation, the control knob 24 is turned to an initial setting, represented by radial lines 28 on the control panel 16 of housing 14, and then sequentially moved to different settings every 1 to 2 minutes or so. If only one or two of the brain wave segments is to be treated, the control knob 24 is operated accordingly. Alternatively, a microprocessor may be set to the automatic mode of operation in which case the microprocessor 30 functions to sequentially shift between the delta, theta, alpha and beta frequency segments at timed intervals.

It is generally accepted that the frequency segments of the brain range in frequency from about 0 to 20 Hz, with the delta segment being in the range of about 0 to 3 Hz, the theta segment about 3 to 8 Hz, the alpha segment about 8 to 12 Hz and the beta segment about 12 to 20 Hz or higher. Respective settings or radial lines 28 on the control panel of housing 14 correspond to specific frequencies within each of these frequency ranges so that each of the delta, theta, alpha and beta segments of the brain can be treated by sequential movement of the control knob 24 to different settings or by operation of the circuit 20 in the microprocessor "automatic" mode. In the presently preferred embodiment, the setting corresponding to the alpha segment frequency range of about 8 to 12 Hz is specifically set at 9.6 Hz.

Solar particles trapped in the ionosphere of the earth are found to resonate at frequencies of about 7.83, 14.1, 20.3, 26.4, 31.32, 39 and 45 Hz, known as the Schumann wave frequencies. In accordance with a principle objective of this invention to provide a therapeutic magnetic field at a flux density and frequencies substantially the same as those occurring in nature, the microprocessor 30 may also be programmed to cause the circuit 20 to produce an output signal which varies in frequency corresponding the Schumann wave frequencies. The magnetic field produced by coils 18A and 18B at such frequencies is believed to be beneficial for the treatment of pain and other conditions while the lower three frequencies double as rTMS brain wave entrainment frequencies.

It is believed that rTMS performed in accordance with the method of this invention is effective in treating and ameliorating symptoms of central nervous system disorders, including, without limitation, Alzheimer's disease, epilepsy, seizure disorder in general, multiple sclerosis, depression, Parkinson's disease, schizophrenia and dementias of various etiologies, migraine headache, cluster headache, recurrent headache syndromes in general, severe pre-menstrual and pre-menopausal syndromes, attention deficit disorders, age-related cognitive and motor deficits, optic nerve atrophy and degenerative diseases of the retina. It is expected that improvements will also be realized in cognitive and motor functions including spatial orientations, sense of balance, improved mobility, memory, alertness, organizational skills and problem solving abilities; improved mood or decreased depression and anxiety; increased endurance, strength and stamina; and improved hand-eye coordination.

A number of subjects have been treated with the device 10 employing the method described herein, as follows.

Case Study 1: A 74 year old fully medicated male was diagnosed 15 years ago with Parkinson's disease, and experienced mild consistent tremor in the right hand, erratic sleep with many sleepless nights, weakness in the arms and legs and moderate to pronounced balance deficit. One 45 minute rTMS session with the inductor coil 18A set to deliver magnetic flux density of about 0.6 gauss at 9.6 Hz applied to back of head resulted in dramatic improvement in balance, speaking volume, strength, motor coordination and sleep patterns. The tremor was reduced significantly to nearly nonexistent. The subject continued the same self-administered treatment, two to three days a week, and over a three month period the subject slowly lost about 25% of the initial benefit at 9.6 Hz. At this point, rTMS sessions employing the coil 18A producing a flux density of 0.6 gauss but sequentially set at delta, theta, alpha and beta frequencies was initiated and applied during rest in bed with the coil 18A placed under 2 pillows behind the back of head delivering approximately 0.2 gauss to the subthalmic region of the brain. Such treatments applied 2–3 times weekly have produced steady improvement in all aspects of motor and cognitive deficit to a new baseline high.

Case 2: A 76 year old, unmedicated male was diagnosed with Parkinson's disease in 1985. The subject experienced severe tremor in both hands, nighttime anxiety requiring several over-the-counter or prescription sleep aids nightly for the past three years, pain in neck, arms, legs and hands, and weakness in the hands, arms and legs. After one 45 minute rTMS session using the coil 18A of this invention operated to produced a 0.6 gauss magnetic flux density at 9.6 Hz applied to back of head under two pillows, the tremor was reduced by about 50%, the subject slept well with no sleeping pills, anxiety was reduced to near nonexistent, mobility in the hands increased dramatically, overall pain was reduced to 25% of baseline and strength in the hips and legs improved by about 30%. This same therapy was continued three times per week for eight weeks, and the subject continued to sleep well with no sleep medication, the tremor in both hands was reduced to about 15% of baseline and strength in the legs and hands further improved. At week 9, rTMS brain wave sessions using the coil 18A operated to produce a 0.6 gauss flux density at delta, theta, alpha and beta frequencies were initiated but applied during rest in bed with the coil 18A placed under the mattress in alignment with the patient's head and yielding approximately 0.1 gauss to the subthalmic region of the brain. Self-administered magnetic brain-wave entrainment for 30 minutes each evening has resulted in further tremor reduction to 5–10% of baseline and reduced incidence of tremor episodes, better mood, clarity of thinking and further improvement in strength and further reduction of overall pain.

Case 3: A 32 year old female, diagnosed with multiple sclerosis in 1992, exhibited symptoms including an erratic signature, poor mood with mild depression, very little energy and the need to walk with a walker. After three, one hour rTMS sessions using the coil 18A operated to produce a 0.7 gauss flux density magnetic field at delta, theta, alpha and beta frequencies, applied to the back of the head, the subject's mood improved, her facial expressions were more animated with better color in the face, her sleep improved with no need for sleep aids, her signature has improved to nearly normal and her leg strength and stamina have improved about 20%.

Case 4: One of two 40 year old identical twin sisters was administered a 45 minute, rTMS session using the coil 18A operated to produce a 0.7 gauss flux density magnetic field at delta, theta, alpha and beta frequencies applied to back of head under two pillows twice weekly. Although both sisters have been diagnosed as border-line schizophrenics, the twin receiving treatment experienced improvements in mood, motivation and well-being, even while engaged in rigorous academic endeavors which, in the past, had exacerbated her symptoms. Their mother has noted a significant improvement in the treated twin, i.e., the schizophrenic episodes have diminished significantly despite her rigorous academic endeavors, while the other twin remains the same.

Case 5: A 62 year old male had been experiencing balance deficit. Two 45 minute sessions using the coil 18A operated to produce a magnetic field with a flux density of 0.6 gauss at 9.6 Hz, located at the back of the head, corrected the balance deficit by about 80%. The subject has continued self administered therapy once per week and reports balance deficit as nearly nonexistent. The subject also reports sleeping sounder and feeling better overall.

Case 6: A 72 year old female had been experiencing balance deficit when ballroom dancing. One 45 minute rTMS session using the coil 18A operated to produce a 0.7 gauss flux density magnetic field set at 9.6 Hz, and applied through one pillow located at the back of head, improved balance significantly while making the subject sleep recognizably better.

Case 6a: A 73 year old male had been experiencing balance deficit when ballroom dancing. One 45 minute rTMS session using the coil 18A operated to produce a magnetic field having a flux density of about 0.7 gauss at 9.6 Hz, and applied through one pillow located at the back of head, improved balance significantly.

Case 7: A 44 year old male experienced balance deficit while walking the seawall behind his property, and while surfing. He also noticed difficulty driving in that he found himself weaving within lanes especially when taking his eyes off of the road even for a couple of seconds. One 45 minute rTMS session using the coil 18A operated to produce a magnetic field having a flux density of about 0.7 gauss at 9.6 Hz, applied to the back of the head, completely eradicated the balance deficit while restoring his driving proficiency especially in regard to not weaving within highway traffic lane lines. After two additional 45 minute rTMS sessions of the same type noted above, the subject's physical endurance/stamina unexpectedly improved by about 25% as measured by specific exercise movements performed to failure.

Case 8: A 52 year old male noticed cognitive deficit relating to balance, coordination and decision making process. One 45 minute rTMS session using the coil 18A operated to produce a 0.6 gauss flux density magnetic field at 9.6 Hz, applied to back of head through a pillow, resulted in significant improvement in balance, hand-eye coordination and thought/decision making processes.

Pain Management and Treatment of Underlying Conditions Causing Pain

It has been found that the device 10 of this invention is useful in the management of pain and the treatment of a variety of conditions which create pain and inflammation, including, without limitation, bone non-union, bone fractures, joint abnormalities and degenerative disorders, spinal or degenerative disk disorders, neuralgia, neuropathy, chronic pelvic pain syndromes, temporomandibular joint disorder ("TMJ"), post-traumatic maxillofacial defects, fibromyalgia, sciatica, spinal cord injuries and resulting neuromuscular deficits, acute pain and inflammation due to arthritis, periarthritis, osteochondrosis, osteoporosis, trauma, chronic ulcers, diabeticneuropathy or circulatory problems, muscle spasms, muscle soreness, muscle stiffness and others. Two types of therapies are performed with the device 10 to treat these conditions, including one with the coil 18A of FIG. 3 and the other with the coil 18B of FIG. 4.

In one presently preferred embodiment, one or more coils 18A are placed beneath the sleeping surface of a patient in general alignment with the head or other area of the body which is experiencing pain or other symptoms to be treated. The coil 18A can be placed under the mattress pad proximal to the injury or under the entire mattress of the sleeping surface. The time varying magnetic field produced by the coil 18A is approximately 0.5 to 1.0 gauss in the immediate area of the coil 18A, and preferably in the range of about 0.01 to 0.1 gauss at the interface of the patient and the sleeping surface directly above the coil 18A, depending upon the thickness of the mattress pad or mattress. Preferably, the patient is exposed continuously to the magnetic field from the coil 18A for a normal sleeping period, e.g. 6 to 8 hours per treatment. The treatment is appropriate for rTMS or to stimulate a wide variety of healing mechanisms in damaged tissues.

Sleeping in the DC, time varying magnetic field generated by the device 10 of this invention is believed to induce the repair and regeneration of many types of physical and neurological injuries, to enhance the efficiency of cellular processes including promoting the body's synthesis of adenosine tri-phosphate and to enhance the blood's ability to carry oxygen. This increases the supply of oxygen and nutrients via the vascular system, improves the removal of waste through the lymphatic system and helps to rebalance the distribution of ions across the cell membrane. Healthy cells in tissue have a membrane potential difference between the inner and outer membrane causing a steady flow of ions through its pores. In a damaged cell, the potential is raised and an increased sodium flow occurs. As a result, interstitial fluid is attracted to the area, resulting in swelling and edema. The application of DC pulsed magnetic fields to damaged cells in accordance with the method of this invention accelerates the reestablishment of normal potentials thus tending to increase the rate of healing while reducing swelling, bruising and inflammation.

The coil 18A, or any array of coils 18A, or in cases of acute injury where coil 18B is employed at night proximal to injury, produce homogenous magnetic waves which expand and collapse radially therefrom with little or no eddy currents to the subject being treated. If two persons sleeping in the same bed are to be treated simultaneously, the coils are preferably located at least 3 feet apart and beneath each of the two sleeping subjects to avoid or reduce the intensity of the intersection of the magnetic field produced by each coil.

Case Study 1: A 44 year old male has been rehabilitating rotator cuff and ligaments in and around hid left shoulder for over 15 years since dislocating the shoulder 3 times during a period of 10 years in sports-related incidents. A coil 18A was placed between the mattress and box spring of the subject's bed, in substantial alignment with the shoulder area, while sleeping. The coil 18A was operated to produce a magnetic field having a flux density of about 0.7 gauss in the area of the coil 18A, and about 0.01 to 0.05 gauss as measured in the area where the subject laid on the bed, at a frequency of 9.6 Hz. After 4 to 5 nights, the constant pain in the shoulder previously experienced by the subject had ended and the subject slept better without being awakened by shoulder pain during the night. By the tenth day, the subject was able to lift weights without the ringing and shooting pain, or the clicking and crunching noises, which he had previously experienced in the left rotator cuff and shoulder ligaments especially while the shoulder was under structural load. Significant improvements in strength and stamina of his upper body during such workouts were evident. The subject has subsequently surfed a number of times and noticed a reduction of all post-session shoulder pain, back pain and neck to nonexistent levels.

Case 2: A 54 year old female complained of attention deficit, a sleep disorder which caused her to awaken at 6 a.m. regardless of what time she went to bed, and persistent weaving in and out of highway lanes while driving. The subject arranged a coil 18A between the mattress and box spring of her bed in general alignment with the back of the head, neck and shoulder area. The coil 18A was operated to produce a magnetic field having a flux density of about 0.7 gauss in the area of the coil 18A, and about 0.01 to 0.05 gauss as measured in the area where the subject's head and neck rested on the bed, at a frequency of 9.6 Hz. After two successive nights of all night therapy, during which time the subject slept deeply for 7 hours, the patient felt noticeably calmer, more focused and she slept better and for longer periods of time. The subject is more comfortable driving and can now take her eyes off of road momentarily without swerving nor is she weaving within lanes. The subject has also in the past suffered from 1–2 migraine headache episodes per month which generally lasted for 2–3 days. The subject reports that upon continued use of the device 10 for 1–3 nights per week, the incidence and severity of migraines have been reduced by at least 80%.

Case 3: A 52 year old male has experienced arthritic pain, rotator cuff, neck and back pain for nearly 10 years. Surfing and spear-fishing significantly exacerbates those symptoms. The subject arranged a coil 18A between the mattress and box spring of his bed in general alignment with the back of the head, neck and shoulder area. The coil 18A was operated to produce a magnetic field having a flux density of about 0.7 gauss in the area of the coil 18A, and about 0.01 to 0.05 gauss as measured in the area where the subject's head and neck rested on the bed, at a frequency of 9.6 Hz. After two all night sessions, the subject experienced approximately a 98% decrease in overall pain which lasted for nearly a week with no additional therapy. Surfing sessions increased from 1 hour to up to 3 hours yet pain remained nearly completely relieved for about one week. Subsequently, the subject reported three weeks later that his overall pain was still only 25% of baseline.

Case 4: A husband suffering from lower back pain, who had 4 back operations in which pins and plates were implanted and who, at time, would rely on a cane for assistance walking, and his wife suffering from tendonitis/bursitis of the elbow and previously wearing an elbow support constantly for 6 months, have been sleeping on a mattress under which a coil 18A was positioned in approximately the center of the bed under the husband's side. The coil 18A was operated to produce a magnetic field having a flux density of about 0.7 gauss in the area of the coil 18A, and about 0.01 to 0.05 gauss as measured in the area where the subjects laid on the bed, at a frequency of 9.6 Hz. They report excellent sleep, the wife remains pain free while the husband has been able to take less-potent, non-habit forming pain medication with further reduction of pain, resulting in increased mobility and no further need for his cane. Husband/wife report wife's migraine episodes have been nearly completely ameliorated since night-time therapy was initiated 6 weeks ago.

Case 5: A husband and wife each 40 years old, initiated sleeping upon coil 18A two days prior to onset of the wife's menstrual cycle. The wife had experienced severe menstrual symptoms for 20 years, and over the previous 18 months such menstrual symptoms worsened due presumably to the onset of menopause. At times, should would be completely debilitated with cramps and migraine headache requiring her for the past several months to take 1–2 days off from work at a time. Her menstrual cycle passed with no migraine headache and minor cramping for the first time in over 20 years.

Case 6: A 62 year old woman experienced knee pain subsequent to knee replacement surgery, resulting in restless sleep. Therapy was initiated by sleeping upon coil 18A for two nights after which time the subject reported better sleep with a 10% reduction in pain. The woman's 10 year old dog which sleeps with her on the bed ceased limping from its recently mended, broken leg.

An alternative method of treatment according to this invention for the management of pain and the treatment of the acute underlying conditions which generate pain, employs the coil 18B depicted in FIG. 4 as part of the device 10. In this embodiment, the coil 18B is placed immediately adjacent the affected areas of the body, i.e., at the location where the pain originates, where the pain is referred, and/or where the condition to be treated is located. Additionally, as noted in case study #15 below, the coil 18B may be located under a sleeping surface as in the treatment method employing the open core coil 18A described above.

Preferably, the patient lies or sits in a comfortable position, with the coil 18B positioned as noted above. The time varying magnetic field produced by the coil 18B has a flux density on the order of about 0.5 to 2.0 gauss at frequencies preferably in the range of 8–11 Hz, and most preferably at 9.6 which is the geomagnetic field of the earth. The duration of the treatment is normally 30 to 60 minutes per session, with the number and frequency of the sessions depending upon the severity of the pain or condition, and the results experienced by the patient. The coil 18B may be moved during the session, as desired, e.g., from the area where the pain is being produced to the area where the pain is referred and visa versa. In most instances, it is preferable to position the coil 18B directly over the pain emanation point initially for about 20–45 minutes, and then move the coil 18B at 5–10 minute intervals to other affected areas such as surrounding nerves, muscles or ligaments.

Case Study 1: A 39 year old female experienced pain in the hip and thigh area due to severe bone/tissue trauma to her left leg in a motorcycle accident 5 years prior. The pain has been recurrent and worsens during changes in weather. The coil 18B was placed in contact with the body over the pain emanation point(s), for one session of about 30 minutes in duration, and operated to produce a magnetic field having a flux density of about 0.7 gauss at 9.6 Hz. The pain was completely eradicated with no further treatment necessary, even though several frontal systems visited the area during the subsequent 4 weeks.

Case 2: A 25 year old male suffered severe trauma to the neck and spine due to a motorcycle accident, resulting in swelling of the spinal cord and loss of all sensation from the chest down. The subject has been confined to a wheelchair with no pain syndromes. The coil 18B was placed in direct contact with the neck, back, hips, knees and feet for approximately 10 minutes each at approximately equal intervals over a one hour period, and operated to produce a magnetic field having a flux density of about 0.9 gauss at 9.6 Hz. During therapy, the subject reported sensations similar to bugs crawling up and down his legs, which was the first sensation the subject had felt below his chest since his accident. Four days post therapy, the patient reported that sensation had partially returned to left calf muscle and hip. Four weeks later the subject reported that he can still feel the touch of a finger to his right calf and hip.

Case 3: A 29 year old female experienced severe TMJ for 3 years involving her neck and muscles of the face. On the morning of the first therapy session, the subject advised she was considering surgery because the pain was unbearable and nothing had relieved or stopped its progression for nearly 3 years. The coil 18B was placed in direct contact with the right side of the patient's neck, first while laying on her back and then her side for approximately one hour, and operated to produce a magnetic field having a flux density of about 0.9 gauss at 9.6 Hz. The subject fell asleep during the therapy on the neck and when she awoke, she was able to open her mouth wide for the first time in over 8 months. Mobility in the neck area improved 90% on her right side, about 70% on her left side and overall pain was reduced by 85–90% from pre-therapy levels.

Case 4: A 38 year old female has been diagnosed with fibromyalgia, which during flare ups, prevent the subject from raising her right elbow above shoulder level. During a recent flare-up while lying prone on her back, the coil 18B was placed in contact with the intersection of the right trapezius muscle and shoulder for 45 minutes, centered over the spine between the shoulders for 10 minutes and then placed at the lumbar region of the spine for 10 minutes. The coil 18B was operated to produce a magnetic field having a flux density of about 0.9 gauss at 9.6 Hz. Upon sitting upright, the subject was able to make full rotation of right arm with no pain, mobility in neck improved by 80–90% and pain in the neck decreased about 85%. The subject's massage therapist confirmed spasms in neck were reduced by 50% immediately after completion of therapy.

Case 5: A 68 year old female was treated complaining of chronic sciatica in right leg. After 15 minutes of therapy with the coil 18B placed at the point where the pain emanated, the discomfort was reduced by about 60%. Massage therapist confirmed spasms in the gluteus maximus muscle were reduced by 30%. The coil 18B was operated to produce a magnetic field having a flux density of about 0.9 gauss at 9.6 Hz.

Case 6: A 28 year old male athlete has experienced lower back pain for several years due to sports activities, and the condition was exacerbated prior to therapy from to three hours of strenuous surfing in sizable waves and strong currents. The coil 18B was placed in direct contact with the back over a one hour period, and operated to produce a magnetic field having a flux density of about 0.9 gauss at 9.6 Hz. The treatment resulted in nearly complete resolution of pain and associated stiffness. On the following morning, the subject played tennis for 2 hours and reported that the back felt much better upon waking, and the relief remained even after playing tennis. Nearly four weeks post-therapy, the subject reports his back pain is still reduced despite surfing several hours twice weekly and playing tennis at least twice weekly.

Case 7: A 54 year old female complained of severe pain in her feet due to ill fitting shoes worn while traveling and hiking through Alaska. The pain syndrome lasted 8 weeks even after taking cortisone shots beginning at week 7. One eight hour therapy session was performed during sleep with the coil 18B placed in the region of the feet under a mattress pad approximately 8–15 cm from soles of her feet. The coil was operated to produce a magnetic field having a flux density of about 0.9 gauss at 9.6 Hz. A resolution of the pain was obtained with the treatment which did not return after at least 12 weeks subsequent to the therapy.

Case 8: A 42 year old male with a history of several back operations which included metal implants in the lumbar region complained of severe lower back pain for several years requiring the use of a cane at times and the constant use of habit forming prescription pain medications on a daily basis. After an initial 2 hour therapy session with the coil 18B placed in direct contact against the lower back and operating to produce a magnetic field having a flux density of 0.9 gauss set at 9.6 Hz, the subject reported significant relief. After 4 therapy sessions of the same duration during a 2 week period, the subject reported tremendous reduction of pain and a significant reduction in his need for pain medications. (See Case Study 4 in previous section).

Case 9: A 40 year old female reported bursitis/tendonitis in her right elbow requiring a brace to be worn most days to reduce pain for several months. After a single 1 hour therapy session in which the coil 18B was placed against the elbow and operated to produce a magnetic field of 0.9 gauss at 9.6 Hz, the subject was pain free for 6 days. Repeated therapy sessions of the same duration for two weeks kept the subject pain free and without need for elbow brace. (See Case Study 4 in previous section).

Case 10: A 40 year old male reported severe lower back pain due to a work related incident. The coil 18B was placed in direct contact with the back over a one hour period, and operated to produce a magnetic field having a flux density of about 0.9 gauss to 9.6 Hz. The subject reported a reduction in pain for 5 days to levels less than experienced in the previous 12 years. He treats himself once per week for several hours while lying on a couch in the same manner noted above, and the pain remains about 70–75% reduced.

Case 11: A 45 year old male reported severe neck pain due to an auto accident, resulting in migraine-like, muscle tension headaches lasting days at a time. During a recent headache episode, the coil 18B was placed in direct contact with the neck over a one hour period, and operated to produce a magnetic field having a flux density of about 0.9 gauss to 9.6 Hz. A complete resolution of the headache episode was obtained.

Case 12: A 60 year old female with a degenerated hip and a candidate for hip replacement experienced moderate back and neck pain with restless sleep. The coil 18B was placed in direct contact with the neck for 45 minutes and lower back, over a 45 minutes during a 90 minute period, and operated to produce a magnetic field having a flux density of about 0.9 gauss at 9.6 Hz. The treatment resulted in nearly complete resolution of pain in neck, back and hip, allowing the patient to sleep. The patient was remarkably pain and medication free for 10 days, and sleep improved to near normal for two weeks.

Case 13: A 49 year old male reported an injury to his hip which occurred during birth, resulting in a crooked walk and in severe hip and knee pain throughout his life. The coil 18B was placed in direct contact with the knee and hip over a 15 minute period, and operated to produce a magnetic field having a flux density of about 0.9 gauss to 9.6 Hz. An 80% reduction of pain was obtained which lasted for 8 days. The same therapy was repeated on two other occasions resulting in a reduction in pain of 75% each time the therapy was repeated. Peak pain during a four week period when therapy was not available was still 50% less than normal.

Case 14: A 70 year old candidate for lumbar fusion, reported severe pain in the lumbar region. The coil 18B was placed in direct contact over the lumbar region for a 45 minute period, and operated to produce a magnetic field having a flux density of about 0.9 gauss to 9.6 Hz. The subject's pain was reduced by about 50% for 48 hours. Two subsequent therapy sessions reduced pain for two days at a time to 50% of baseline.

Case 15: A 59 year old female with a neurodegenerative disease experienced daily moderate to sever pain and weakness in the legs. The coil 18B was placed in direct contact with the legs, feet and knees over a period of three hours, and operated to produce a magnetic field having a flux density of about 0.9 gauss at 9.6 Hz. After a 3 hour self therapy session, the subject experienced a reduction in pain of about 70% and the weakness in her legs was reduced by about 25%. The relief lasted for several days.

Case 16: Two sisters 68 and 69 years old were diagnosed with rheumatoid arthritis over two decades ago, each with progressive inflammatory joint destruction resulting in deformity in the ankles, feet and hands. Each received a single hour of therapy to the base of the spine/lower back. Immediately following therapy, the 69 year old reported overall reduction of pain to 30% of baseline, and the 68 year old reported overall pain reduced to 25% of baseline. Ambulation in both significantly improved.

Although the therapies performed with the coils 18A and 18B have been described separately above, it is contemplated that both may be used by patients as part of an overall treatment regime. For example, a patient may undergo a 30 to 60 minute session with the coil 18B applied directly to pain emanation points followed by treatment with the coil 18A under the mattress for several hours while sleeping. The beneficial results from such combined therapy are cumulative and synergistic effects have been observed including improved quality of sleep which benefits the person's appearance and well being.

While the invention has been described with reference to a preferred embodiment, it should be understood by those skilled in the art that various changes may be made and equivalents substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. The method of treating psychological, neurological and central nervous system disorders of a patient, comprising:
   (a) positioning a magnetic flux generating coil coupled to a circuit in the proximity of the head of a patient;
   (b) operating the circuit to produce a pulsed, DC output to the magnetic flux generating coil;
   (c) exposing the head of the patient to a time varying magnetic field from the magnetic flux generating coil having a frequency in the range of about 0 to 45 Hz and a flux density in the range of about 0.0001 to 2.0 gauss.

2. The method of claim 1 in which step (a) comprises positioning the magnetic flux generating coil in the range of about 5 to 10 cm from the head of the patient.

3. The method of claim 1 in which step (c) comprises exposing the head of the patient to a time varying magnetic field from the magnetic flux generating coil having a frequency in the range of about 8 to 11 Hz.

4. The method of claim 1 which step (c) comprises exposing the head of the patient to a time varying magnetic field from the magnetic flux generating coil having a frequency of about 9.6 Hz.

5. The method of claim 1 in which step (c) comprises exposing the head of the patient to a time varying magnetic field from the magnetic flux generating coil having a flux density in the range of about 0.5 to 1.0 gauss.

6. The method of claim 1 in which step (c) comprises exposing the head of the patient to a time varying magnetic field from the magnetic flux generating coil having frequencies substantially equal to the delta, theta, alpha and beta frequencies of the patient's brain.

7. The method of claim 1 in which step (c) comprises exposing the head of a patient to a time varying magnetic field from the magnetic flux generating coil having frequencies substantially equal to terrestrially occurring Schumann wave frequencies.

8. The method of claim 1 further including the step of:
(d) maintaining the exposure of step (c) for a period of about 30 minutes to 60 minutes in a single treatment session.

9. The method of claim 1 in which step (a) comprises positioning a non-conductive inductor coil having an open center.

10. The method of treating physical and mental disorders of a patient, comprising:
(a) positioning a magnetic flux generating coil coupled to a circuit beneath the sleeping surface of a patient;
(b) operating the circuit to produce a pulsed, DC output to the magnetic flux generating coil;
(c) directing a time varying magnetic field from the magnetic flux generating coil through the sleeping surface to a patient resting upon the sleeping surface for a period of about 4 to 8 hours in a single treatment session, the magnetic field having a frequency in the range of about 0.5 to 45 Hz and a flux density measured at the area of contact between the patient and the sleeping surface in the range of about 0.1 to 0.4 gauss.

11. The method of claim 10 in which step (a) comprises positioning the magnetic flux generating coil beneath the sleeping surface in substantial alignment with the head of a patient resting on the sleeping surface.

12. The method of claim 10 in which step (a) comprises positioning the magnetic flux generating coil beneath the sleeping surface in alignment with damaged neurological tissues or bodily tissues or bone of a patient resting on the sleeping surface.

13. The method of claim 10 in which step (c) comprises directing a time varying magnetic field having a frequency in the range of about 8 to 11 Hz.

14. The method of claim 10 in which step (c) comprises exposing the head of the patient to a time varying magnetic field from the magnetic flux generating coil having a frequency of about 9.6 Hz.

15. The method of claim 10 in which step (c) comprises directing a time varying magnetic field having a flux density in the range of about 0.01 to 0.1 gauss.

16. The method of claim 10 in which step (c) comprises directing a time varying magnetic field from the magnetic flux generating coil to the patient having frequencies substantially equal to the delta, theta, alpha and beta frequencies of the patient's brain.

17. The method of claim 10 in which step (c) comprises directing a time varying magnetic field from the magnetic flux generating coil to the patient having frequencies substantially equal to terrestrially occurring Schumann wave frequencies.

18. The method of claim 10 in which step (a) comprises positioning a non-conductive inductor coil having an open center.

19. The method of claim 10 in which step (a) comprises positioning a magnetic field generating coil having a non-conductive inductor coil with an open center.

20. The method of claim 10 in which step (a) comprises positioning an inductor coil having a ferrous care.

21. The method of treating physical and mental disorders of a patient, comprising:
(a) positioning an array of magnetic flux generating coils coupled to a circuit beneath the sleeping surface of a patient, each of said magnetic flux generating coils having a non-conductive inductor coil with an open center;
(b) operating the circuit to produce a pulsed, DC output to the magnetic flux generating coils;
(c) directing a time varying magnetic field from the magnetic flux generating coils through the sleeping surface to a patient resting upon the sleeping surface, the magnetic field having a frequency in the range of about 0.5 to 45 Hz and a flux density measured at the area of contact between the patient and the sleeping surface in the range of about 0.1 to 0.4 gauss.

* * * * *